United States Patent [19]

Girotra et al.

[11] Patent Number: 4,816,477
[45] Date of Patent: Mar. 28, 1989

[54] ANTIHYPERCHOLESTEROLEMIC β-LACTONES

[75] Inventors: Narindar N. Girotra, Parlin; Shu S. Yang, Bridgewater; Donald W. Graham, Mountainside, all of N.J.

[73] Assignee: Merck & Co., Inc., Rahway, N.J.

[21] Appl. No.: 53,646

[22] Filed: May 26, 1987

[51] Int. Cl.$^4$ ............... A61K 31/365; C07D 305/08; C07D 305/12
[52] U.S. Cl. ................... 514/449; 549/263; 549/327; 549/328
[58] Field of Search ..................... 549/263, 327, 328; 514/449

[56] References Cited

U.S. PATENT DOCUMENTS 4,358,602 11/1982 Umezawa et al. ............ 549/328
4,598,089 7/1986 Hadvary et al. .............. 549/263
4,751,237 6/1988 Chabala et al. ............... 514/449

FOREIGN PATENT DOCUMENTS 0185359 6/1986 European Pat. Off. ........ 549/328

OTHER PUBLICATIONS

Chemical Communications, 1970, p. 639 [(Chem. Abstracts; vol. 73 #55594j (1970)].
J. Chem. Soc. (c), 1971, pp. 3888–3891 [(Chem. Abstracts; vol. 76, #45686 p. (1972)].

Primary Examiner—Glennon H. Hollrah
Assistant Examiner—Susan P. Treanor
Attorney, Agent, or Firm—Joseph F. DiPrima; Michael C. Sudol

[57] ABSTRACT

The compounds of the following structural formula (I)

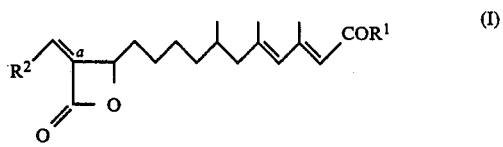

ar 3-hydroxy-3-methylglutaryl-coenzyme A (HMG-CoA) synthase inhibitors and useful as antihypercholesterolemic agents for the treatment of disease in which the inhibition of cholesterol biosynthesis would be useful, such as arteriosclerosis, hyperlipidemia and familial hypercholesterolemia.

19 Claims, No Drawings

ANTIHYPERCHOLESTEROLEMIC β-LACTONES

BACKGROUND OF THE INVENTION

The compound of the formula (I), wherein $R^1$ and $R^2$ are hydroxy and a represents a single bond, 12-hydroxy-13-hydroxymethyl-3,5,7-trimethyltetradeca-2,4-dien-1,14-dioic acid 12,14-lactone, was identified as an antibiotic fungal metabolite in 1970 [Aldridge et al., Chem. Comm., 1970, p. 639]. The compounds of the formula (I), wherein $R^1$ is methoxy and $R^2$ is hydroxy and the tetrahydro analog wherein $R^1$ and $R^2$ are hydroxy were disclosed in the structure elucidation of the compound of the formula (I) wherein $R^1$ and $R^2$ are hydroxy [Aldridge et al. J. Chem. Soc. (C), 1971, pp. 3888-3891].

Additionally, co-pending patent application Ser. No. 856,316, filed Apr. 28, 1986 is directed to the antihypercholesterolemic utility of these known compounds and co-pending patent application Ser. No. 021,848, filed Mar. 4, 1987 discloses novel β-lactone derivatives and their antihypercholesterolemic utility.

SUMMARY OF THE INVENTION

This invention relates to the novel compounds of the formula (I) and the pharmacological properties of these compounds which have been found to be HMG-CoA synthase inhibitors and useful as antihypercholesterolemic agents either as the sole therapeutic agent or in combination with bile acid sequestrants.

DETAILED DESCRIPTION OF THE INVENTION

The present invention is directed to novel compounds represented by the following general structural formula (I):

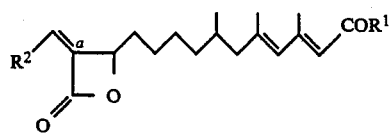

wherein:
$R^1$ is selected from
(1) hydroxy,
(2) $C_{1-6}$ alkoxy,
(3) substituted $C_{1-6}$ alkoxy in which the substituent is a phenyl group,
(4) amino,
(5) $C_{1-6}$ alkylamino,
(6) substituted $C_{1-6}$ alkylamino in which the substituent is a hydroxy group,
(7) phenylamino,
(8) substituted phenylamino in which the substituent is a fluoro, chloro, or bromo, and
(9) (2-thio)-pyridine;
$R^2$ is selected from
(1) hydrogen,
(2) halogen,
(3) cyano,
(4) azido, and
(5) $C_{1-6}$ alkylcarbonylthio,
a represents a single bond or a double bond,
and pharmaceutically acceptable salts thereof.

One embodiment of the compounds of the present invention is the class of compounds of the formula (I) wherein $R^2$ is hydrogen and a is a single bond. Exemplifying this embodiment are the following compounds:
(1) 11-(3-methyl-4-oxo-2-oxetano)-3,5,7-trimethyl-2,4-undecadienoic acid; and
(2) methyl 11-(3-methyl-4-oxo-2-oxetano)-3,5,7-trimethyl-2,4-undecadienoate;

A second embodiment of the compounds of the present invention is the class of compounds of the formula (I) wherein $R^2$ is halogen and a is a single bond. A specific subclass of this embodiment are the compounds of the formula (I) wherein $R^1$ is hydroxy. Exemplifying this subclass are the following compounds:
(1) 11-(3-chloromethyl-4-oxo-2-oxetano)-3,5,7-trimethyl-2,4-undecadienoic acid;
(2) 11-(3-bromomethyl-4-oxo-2-oxetano)-3,5,7-trimethyl-2,4-undecadienoic acid; and
(3) 11-(3-fluoromethyl-4-oxo-2-oxetano)-3,5,7-trimethyl-2,4-undecadienoic acid.

A third embodiment of the compounds of the present invention is the class of compounds of the formula (I) wherein $R^2$ is cyano and a is a single bond. A specific subclass of this embodiment are the compounds of the formula (I) wherein $R^1$ is $C_{1-6}$ alkoxy. Exemplifying this subclass is the following compound:
(1) methyl 11-(3-cyanomethyl-4-oxo-2-oxetano)-3,5,7-trimethyl-2,4-undecadienoate.

A fourth embodiment of the compounds of the present invention is the class compounds of the formula (I) wherein $R^2$ is azido and a is a single bond. A specific subclass of this embodiment are the compounds of the formula (I) wherein $R^1$ is $C_{1-6}$ alkoxy. Exemplifying this subclass is the following compound:
(1) methyl 11-(3-azidomethyl-4-oxo-2-oxetano)-3,5,7-trimethyl-2,4-undecadienoate.

A fifth embodiment of the compounds of the present invention is the class of compounds of the formula (I) wherein $R^2$ is $C_{1-6}$ alkylcarbonylthio and a is a single bond. A specific subclass of this embodiment are the compounds of the formula (I) wherein $R^1$ is $C_{1-6}$ alkoxy. Exemplifying this subclass is the following compound:
(1) methyl 11-(3-acetylthiomethyl-4-oxo-2-oxetano)-3,5,7-trimethyl-2,4-undecadienoate.

Another embodiment of the compounds of the present invention is the class of compounds of the formula (I) wherein $R^2$ is hydrogen and a is a double bond. A specific subclass of this embodiment are the compounds of the formula (I) wherein $R^1$ is hydrogen or $C_{1-6}$ alkoxy. Exemplifying this subclass is the following compound:
(1) 11-(3-methylene-4-oxo-2-oxetano)-3,5,7-trimethyl-2,4-undecadienoic acid; and
(2) methyl 11-(3-methylene-4-oxo-2-oxetano)-3,5,7-trimethyl-2,4-undecadienoate.

The present invention is also directed to a method of inhibiting cholesterol biosynthesis which comprises the administration to a subject in need of such treatment a nontoxic therapeutically effective amount of a compound represented by the following general structural formula (I) and pharmaceutically acceptable salts thereof.

The present invention is also directed to a method of inhibiting the activity of HMG-CoA synthase enzyme which comprises the administration to a subject in need of such treatment a nontoxic therapeutically effective amount of a compound represented by the general structural formula (I) and pharmaceutically acceptable salts thereof. Specifically the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 20 mg to 2000 mg (preferably 20 to 100 mg) which may be given in two to four divided doses. Hiher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic HMG-CoA synthase inhibition activity of the compounds of this invention is measured by the standard in vitro protocol described below:

The livers from male Charles River CD rats (225-350 g) were homogenized in 0.25 M sucrose which was adjusted with phenylmethylsulfonylfluoride (PMSF) and N-p-tosyl-1-lysine chloromethyl ketone (TLCK) so that the final concentration of each was 50 and 25 mg/ml, respectively. The homogenate was centrifuged at 15,000×g for 20 minutes, the supernatant filtered through a fine nylon screen to remove most of the fat layer and recentrifuged at 100,000×g for 1 hour. This supernatant was removed and 1 M potassium phosphate, dithiothreitol (DTT) and ethylene glycol-bis($\beta$-aminoethyl ether)-N,N,N',N'-tetraacetic acid (EGTA) added to give a final concentration of 0.1 M (pH 7.2), 0.5 mM and 0.1 mM, respectively. Solid ammonium sulfate was added to 50% saturation to the protein solution, it was centrifuged at 15,000×g and the supernatant discarded. This precipitated protein could be stored at −70° C. for at least one month with very little loss of activity. The ammonium sulfate precipitate was dissolved in an minimal amount of 0.06 M potassium phosphate buffer (pH 7.2) containing 0.5 mM dithiothreitol and 0.1 mM EGTA (referred to as 0.06 M phosphate buffer) and dialyzed overnight against 2 liters of the same buffer to remove the ammonium sulfate and to inactivate HMG-CoA lyase [Clinkenbeard, et al., J. Biol. Chem. 250, 3108–3116(1975)].

The dialyzed extract was added to a column of DEAE-52 (Whatman) which had been equilibrated with 0.06 M phosphate buffer (10 mg of protein to 1 ml bed volume of the resin). The DEAE-cellulose was eluted with 0.06 M phosphate buffer until the optical density at 280 nm was essentially zero. This fraction contained the $\beta$-ketoacetyl-CoA thiolase activity. The HMG-CoA synthase was eluted from the column with 0.1 M phosphate buffer (pH 7.2) containing 0.5 mM DTT and 0.1 mM EGTA, and was virtually free of all thiolase activity. The protein was precipitated by the addition of ammonium sulfate to give 50% saturation. This solution was stirred for 10 minutes at 4° C. and the precipitate collected by centrifugation at 15,000 rpm for 10 minutes. The supernatant was discarded and the precipitate dissolved in a minimum of 0.06 M phosphate buffer, pH 7.2 (about 10 ml) and the enzyme stored at −80° C.

HMG-CoA Synthase Inhibition Assay

Enzyme protein (ca. 24 mg) was added to a solution containing 117 mM Tris-HCl (pH 8.0), 11.7 mM MgCl$_2$, 1.17 mM ethylenediaminetetraacetic acid (EDTA), 0.58 mM dithiothreitol, and the indicated concentrations of the test compound (added as a 2 mg/ml solution in dimethylsulfoxide). The incubation took place in a volume of 0.085 ml at 30° in a shaking water bath. After 5 minutes, 15 ml of a solution containing acetoacetyl-CoA and 0.1 μCi of 1-[$^{14}$C]-acetyl-CoA was added to give a final concentrations of 0.1 and 0.4 μM, respectively. The incubation was continued for 10 more minutes and the reaction stopped by the addition of 50 ml of the assay mixture to 0.2 ml of 6N HCl in a glass scintillation vial. The vial was heated for 1 hour at 120° after which time 0.2 ml more of 6N HCl was again added to each vial and the heating continued for another hour. Following this, 1.0 ml of 0.9% saline was added to each vial and finally 10 ml of scintillation liquid. Radioactivity was determined in a Packard Tri-Carb liquid scintillation counter. Percent inhibition is calculated by the formula:

$$1 - \frac{\text{Sample} - \text{Blank}}{\text{Control} - \text{Blank}}$$

IC$_{50}$ values were determined by plotting the log of the concentration of the test compound verses the percentage inhibition and fitting a straight line to the resulting data by using the least squares method.

Representative of the intrinsic HMG-CoA synthase inhibitory activities of the compounds of this invention, tabulated below are the IC$_{50}$ or IC$_{25}$ (the inhibitory concentration which inhibits 50 percent and 25 percent of the HMG-CoA synthase activity respectively).

| Compounds of the Formula (I) | | |
|---|---|---|
| R$^1$ | R$^2$ | IC$_{50}$ |
| OH | H | $10^{-7}$ |
| OCH$_3$ | H | $(6 \times 10^{-6} \text{ M})^1$ |
| OH | Cl | $3 \times 10^{-7}$ M |
| OH | Br | $1.4 \times 10^{-6}$ M |
| OH | F | $2.8 \times 10^{-7}$ M |
| OCH$_3$ | CN | $2.9 \times 10^{-6}$ M |
| OCH$_3$ | N$_3$ | $10^{-7}$ M |
| OCH$_3$ |  | $(10^{-5} \text{ M})^2$ |

[1]22.7 percent inhibition
[2]47.9 percent inhibition

The compounds of the formula (I) wherein R$^2$ is hydrogen or halogen and a is a single bond are conveniently prepared from the appropriately substituted compound of the formula (I) wherein R$^1$ and R$^2$ are hydroxy and a is a single bond by the formation of the C$_{1-6}$ alkyl ester analog followed by the replacement of the hydroxy moiety with a halogen to give the halo methyl derivative, $R^2$ is halogen, which can then reduced with tributyltin hydride to yield the compounds of the formula (I) wherein $R^2$ is hydrogen. If the free acid of the formula (I) ($R^1$ is hydroxy) is desired the ester function is removed under mild hydrolytic condition either before reduction for the compounds of the formula (I) wherein $R^2$ is halogen or after reduction for the compounds of the formula (I) wherein $R^2$ is hydrogen.

The compounds of the formula (I) wherein $R^2$ is cyano are conveniently prepared from the appropriately substituted compound of the formula (I) wherein $R^2$ is hydroxy and $R^1$ is alkoxy and a is a single bond by forming the methanesulfonyloxy derivative and then displacing the methanesulfonyloxy group with a cyano anion from an alkali metal cyanide, such as sodium cyanide. If the free acid of the formula (I) ($R^1$ is hydroxy) is desired the appropriately substituted ester is hydrolyzed under mild conditions.

The compounds of the formula (I) wherein $R^2$ is azido are conveniently prepared from the compounds of the formula (I) wherein $R^2$ is methanesulfonyloxy by the reaction with an alkali metal azide, such as sodium azide or from compounds of the formula (I) wherein $R^2$ is hydrOxy by reaction with an alkali metal azide, triphenylphosphine and dialkoxycarbonylazodicarboxylate.

The compounds of the formula (I) wherein $R^2$ is $C_{1-6}$ alkylcarbonylthio are conveniently prepared from the compounds of the formula (I) wherein $R^2$ is methanesulfonyloxy by the reaction with an alkali metal thiolcarboxylate, such as potassium thiolacetate or from the compounds of the formula (I) wherein $R^2$ is hydroxy by reaction with an alkali metal thiolcarboxylate, triphenylphosphine and a dialkoxycarbonylazodicarboxylate.

The compounds of the formula (I) wherein a is a double bond are readily prepared by the elimination of the methanesulfonyloxy group from the appropriately substituted derivatives of the compounds of the formula (I) under mild basic conditions.

The following examples illustrate the preparation of the compounds and their incorporation into pharmaceutical compositions and as such are not to be construed as limiting the invention set forth in the claims appended hereto.

EXAMPLE 1

Preparation of 11-(3-Chloromethyl-4-oxo-2-oxetano)-3,5,7-trimethyl-2,4-undecadienoic acid (a) tert-Butyl 11-(3-hydroxymethyl-4-oxo-2-oxetano)-3,5,7-trimethyl-2,4-undecanoate (1a)

Three portions of O-t-butyl-N,N'-diisopropylisourea (200 mg) were added at 3 hour intervals to a solution of the compound from 11-(3-hydroxymethyl-4-oxo-2-oxetano)-3,5,7-trimethyl-2,4-undecadienoic acid (310 mg, 0.96 mmol) in methylene chloride (2.5 ml) at room temperature. After stirring for an additional 16 hours, the solids were filtered and washed twice with methylene chloride. The residue after evaporation in vacuo was purified by preparative thin layer chromatography to afford the desired product.

NMR (CDCl$_3$)$\delta$1.50 (s,9H), 3.41 (d of t, 1H), 3.8-4.1 (m, 2H), 4.58 (m, 1H) IR 1820 cm$^{-1}$, 1703 cm$^{-1}$.

(b) tert-Butyl 11-(3-chloromethyl-4-oxo-2-oxetano)-3,5,7-trimethyl-2,4-undecanoate (1b)

A mixture of the compound (1a) (18 mg) and polymer supported triphenylphosphine (40 mg) in carbon tetrachloride (0.5 ml) was stirred and heated under reflux in a nitrogen atmosphere for 1 hour. The resin was filtered and washed with ethyl acetate (3×). Evaporation in vacuo and TLC purification (silica gel, 7% MeOH-CH$_2$Cl$_2$) gave the desired product. NMR $\delta$ 1.51 (s, 9H, OC(CH$_3$)$_3$), 3.61 (m, 1H, 13-H), 3.82 (m, 2H, CH$_2$Cl), 4.51 (m, 1H, 12-H).

(c) 11-(3-Chloromethyl-4-oxo-2-oxetano)-3,5,7-trimethyl-2,4-undecadienoic acid

A solution of the compound (1b) (7 mg) in 10% trifluroacetic acid —CH$_2$Cl$_2$ (300 μl) was kept at room temperature for 1.5 hours. After cooling in an ice bath and dilution with 1 ml each of ice cold CH$_2$Cl$_2$ and H$_2$O, the aqueous phase was extracted with CH$_2$Cl$_2$ (2×), and the combined organic extracts were washed with H$_2$O and dried (MgSO$_4$). Evaporation in vacuo and purification by TLC (silica gel, 7% MeOH-CH$_2$Cl$_2$) gave the desired product.

NMR $\delta$ 3.62 (m, 1H, 13-H), 3.81 (m, 2H, CH$_2$Cl$_2$), 4.51 (m, 1H, 12-H).

EXAMPLE 2

Preparation of 11-(3-bromomethyl-4-oxo-2-oxetano)-3,5,7-trimethyl-2,4-undecadienoic acid A solution of triphenylphosphine (Ph$_3$P) (31 mg, 0.118 mmoles) in THF (0.2 ml) was added dropwise with vigorous stirring at room temperature to a solution of N-bromosuccinamide (NBS) (21 mg, 0.118 mmoles). To the suspension was added a solution of the compound (1a) (43 mg, 0.117 mmoles) in THF (0.2 ml). After stirring at room temperature for 1 hour, NBS (4 mg) and Ph$_3$P (6 mg) were added. After stirring for 2 hours more, the solid was filtered and washed with THF (3×). The filtrate was purified by TLC (hexane EtOAc 9:1, silica gel) to give the tert-butyl ester of the desired product.

NMR $\delta$ 1.50 (s, 9H, OC(CH$_3$)$_3$), 3.65 (m, 3H, CH$_2$Br+13-H), 4.46 (m, 1H, 13-H).

Removal of the tert-butyl group was accomplished by the same procedure of Example (1c) and gave the desired product.

NMR $\delta$ 3.63 (m, 3H, CH$_2$Br+13-H), 4.44 (m, 1H, 12-H).

EXAMPLE 3

Preparation of 11-(3-fluoromethyl-4-oxo-2-oxetano)-3,5,7,-trimethyl-2,4-undecadienoic acid To a solution of diethylaminosulfur trifluoride (25 μl, 0.20 mmole) in CH$_2$Cl$_2$ (125 ml) cooled to −78° was added dropwise over 5 minutes with magnetic stirring in a N$_2$ atmosphere a solution of the compound (1a) (57 mg, 0.15 mmole) in CH$_2$Cl$_2$ (125 μl). After 5 minutes the mixture was allowed to warm to room temperature (approx. 15 minutes), cooled to 0° and quenched with 0.5 ml of saturated NaHCO$_3$ solution. After dilution with CH$_2$Cl$_2$ and H$_2$O, the aqueous phase was extracted with CH$_2$Cl$_2$ (3×). The combined CH$_2$Cl$_2$ phases were washed with H₂O and dried (MgSO₄). Purification of TLC (silica gel hexane-EtOAc 4:1) gave the tert butyl ester of the desired product. NMR δ 1.50 (S, 9H, OC(CH₃)₃), 3.54 (m, 1H, 13-H), 4.5–5.0 (m, 3H, CH₂F+12-H).

Removal of the tert-butyl group was accomplished by the same procedure of Examples (1c) and gave the desired product.

NMR δ 3.54 (m, 1H, 13-H), 4.5–5.0 (m, 3H, CH₂F+12-H).

EXAMPLE 4

Preparation of 11-(3-methyl-4-oxo-2-oxetano)-3,5,7-trimethyl-2,4-undecadienoic acid A solution of the compound of Example (1a) (25 mg, 0.058 mmoles) and nBu₃SnH (24 μl, 0.087 mmoles) in toluene (250 ml) was warmed at 55° for 4 hours in a N₂ atmosphere. The cooled reaction mixture was purified by TLC (silica gel, hexane-EtOAc 9:1) to give the tert-butyl ester of the desired compound. NMR δ 1.49 (s, 9H, OC(CH₃)₃), 1.39 (d, 3H, 13-CH₃), 3.23 (dxq, 1H, 13-H), 4.16 (m, 1H, 12-H).

Removal of the tert-butyl was accomplished by the same procedure of Example (1c) and gave the desired product. NMR δ 1.39 (d, 3H, 13-CH₃), 3.23 (dxq, 1H, 13-H), 4.18 (m, 1H, 12-H).

EXAMPLE 5

Preparation of methyl 11-(3-cyanomethyl-4-oxo-2-oxetano)-3,5,7-trimethyl-2,4-undecadienoate (a) Methyl 11-(3-methanesulfonyloxy-methyl-4-oxo-2-oxetano)-3,5,7-trimethyl-2,4-undecadienoate (5a)

To a solution of methyl 11-(3-hydroxymethyl-4-oxo-2-oxetano)-3,5,7-trimethyl-2,4-undecadienoate (100 mg) and triethylamine (150 mg) in methylene chloride (5 ml) at 0° C. to 5° C. was added a solution of methanesulfonyl chloride (150 mg) in methylene chloride (0.5 ml) during 10 minutes. The mixture was stirred at 0° to 5° for ½ hour and then at room temperature for ½ hour. The desired product was isolated via Preparative TLC purification. 200 MHz NMR δ 3.08 ppm (s, 3H, CH₃SO₃—).

(b) Methyl 11-(3-cyanomethyl-4-oxo-2-oxetano)-3,5,7-trimethyl-2,4-undecadienoate (5b)

To a solution of the compound (5a) (10 mg) in dimethyl sulfoxide (0.5 ml) and dimethoxymethane (0.5 ml) at 5° C. was added a solution of sodium cyanide (0.9 mg) in dimethyl sulfoxide (0.3 ml) during 10 minutes. The mixture was stirred at 5° for 17 hours. Purification of the reaction mixture via preparative TLC gave the desired product.

EXAMPLE 6

Preparation of methyl 11-(3-acetylthiomethyl-4-oxo-2-oxetano)-3,5,7-trimethyl-2,4-undecadienoate Diisopropyl azodicarboxylate (0.052 ml, 0.266 mmole) was added to a stirred solution of triphenylphosphine (0.07 g, 0.266 mmole) in dry THF (0.5 ml) at reflux under nitrogen. The mixture was stirred for 2 hours. To the stirred mixture was then added to a solution of methyl 11-(3-hydroxymethyl-4-oxo-2-oxetano)-3,5,7-trimethyl-2,4-undecadienoate (0.045 g, 0.133 mmole) and thiolacetic acid (0.02 ml, 0.266 mmole) in THF (1 ml). After 1 hour at reflux. and 2 hours at ambient temperature, the mixture was purified via preparative thin layer chromatography (tlc) on silica gel eluted with EtOAc:hexane (20:80) to afford the desired product.

EXAMPLE 7

Preparation of methyl 11-(3-azidomethyl-4-oxo-2-oxetano)-3,5,7-trimethyl-2,4-undecadienoate Diphenylphosphine azide (0.043 ml, 0.2 mmole) was added to a stirred solution of methyl 11-(3-hydroxymethyl-4-oxo-2-oxetano)-3,5,7-trimethyl-2,4-undecadienoate (0.034 g, 0.1 mmole) and triphenylphosphine (0.053 g, 0.2 mmoles) in dry THF (0.6 ml) at reflux under nitrogen. Diisopropylazodicarboxylate (0.04 ml) was added to the mixture and after 1 hour at reflux and 1 hour at ambient temperature, the mixture was purified via preparative tlc on silica gel eluted with EtOAc:hexane (15:85) to afford the desired product.

EXAMPLE 8

Preparation of methyl 11-(3-methylene-4-oxo-2-oxetano)-3,5,7-trimethyl-2,4-undecadienoate Utilizing the procedure of Example 5, Step (a) the above titled compound was also prepared and isolated as a minor component.

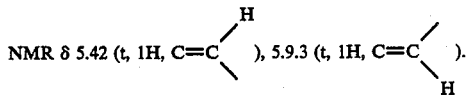

The above titled product was also prepared and isolated as a minor component utilizing the procedure of Example 5, Step (b).

EXAMPLE 9

Preparation of Alkali and Alkaline Earth Salts of Compound I wherein R¹ is hydroxide To a solution of the lactone from Example 1 (42 mg) in ethanol (2 ml) is added aqueous NaOH (1 equivalent). After one hour at room temperature, the mixture is taken to dryness in vacuo to yield the sodium salt of Compound I, wherein R¹ is hydroxy.

In like manner, the potassium salt is prepared using one equivalent of potassium hydroxide, and the calcium salt using one equivalent of CaO.

EXAMPLE 10

As a specific embodiment of an oral composition of a compound of this invention, 20 mg of the lactone from Example 1 is formulated with sufficient finely divided lactose to provide a total amount of 580 to 590 mg to fill a size 0 hard gelatin capsule.

EXAMPLE 11

As a specific embodiment of a parenteral composition of a compound of this invention, 20 mg of the lactone from Example 1, as the sodium salt, is dissolved in sterile water, buffered to a pH of 7 with 1.0 mM potassium phosphate buffer solution to a concentration of 2.0 percent and is placed in a sterile ampule for parenteral administration.

What is claimed is:

1. A compound represented by the following structural formula (I):

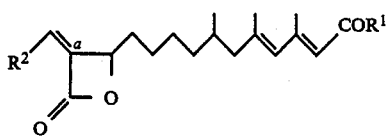

wherein:
R¹ is selected from
   (1) hydroxy,
   (2) $C_{1-6}$ alkoxy,
   (3) substituted $C_{1-6}$ alkoxy in which the substituent is a phenyl group,
   (4) amino,
   (5) $C_{1-6}$ alkylamino,
   (6) substituted $C_{1-6}$ alkylamino in which the substituent is a hydroxy group,
   (7) phenylamino,
   (8) substituted phenylamino in which the substituent is a fluoro, chloro, or bromo;
R² is selected from
   (1) hydrogen,
   (2) halogen,
   (3) cyano,
   (4) azido, and
   (5) $C_{1-6}$ alkoxycarbonylthio;
a represents a single bond or a double bond,
and pharmaceutically acceptable salts thereof.

2. A compound of claim 1 wherein R² is hydrogen and a is a single bond.

3. A compound of claim 2 which is 11-(3-methyl-4-oxo-2-oxetano)-3,5,7-trimethyl-2,4-undecadienoic acid.

4. A compound of claim 2 which is methyl 11-(3-methyl-4-oxo-2-oxetano)-3,5,7-trimethyl-2,4-undecadienoate.

5. A compound of claim 1 wherein R² is halogen and a is a single bond.

6. A compound of claim 5 which is 11-(3-chloromethyl-4-oxo-2-oxetano)-3,5,7-trimethyl-2,4-undecadienoic acid.

7. A compound of claim 5 which is 11-(3-bromomethyl-4-oxo-2-oxetano)-3,5,7-trimethyl-2,4-undecadienoic acid.

8. A compound of claim 5 which is 11-(3-fluoromethyl-4-oxo-2-oxetano)-3,5,7-trimethyl-2,4-undecadienoic acid.

9. A compound of claim 1 wherein R² is cyano and a is a single bond.

10. A compound of claim 9 which is methyl 11-(3-cyanomethyl-4-oxo-2-oxetano)-3,5,7-trimethyl-2,4-undecadienoate.

11. A compound of claim 1 wherein R² is azido and a is a single bond.

12. A compound of claim 11 which is methyl 11-(3-azidomethyl-4-oxo-2-oxetano)-3,5,7-trimethyl-2,4-undecadienoate.

13. A compound of claim 1 wherein R² is $C_{1-6}$ alkylcarbonylthio and a is a single bond.

14. A compound of claim 13 which is methyl 11-(3-acetylthiomethyl-4-oxo-2-oxetano)-3,5,7-trimethyl-2,4-undecadienoate.

15. A compound of claim 1 wherein R² is hydrogen and a is a double bond.

16. A compound of claim 15 which is 11-(3-methylene-4-oxo-2-oxetano)-3,5,7-trimethyl-2,4-undecadienoic acid.

17. A compound of claim 15 which is methyl 11-(3-methylene-4-oxo-2-oxetano)-3,5,7-trimethyl-2,4-undecadienoate.

18. A pharmaceutical composition for the treatment of hypercholesterolemia which comprises a non-toxic effective amount of a compound of claim 1 and a pharmaceutically acceptable carrier.

19. A method of inhibiting cholesterol biosynthesis which comprises the administration to a subject in need of such treatment a non-toxic therapeutically effective amount of a compound of claim 1.

* * * * *